US009526696B2

(12) United States Patent
Montgomery

(10) Patent No.: US 9,526,696 B2
(45) Date of Patent: *Dec. 27, 2016

(54) FORMULATIONS OF AMINOGLYCOSIDE AND FOSFOMYCIN COMBINATIONS AND METHODS AND SYSTEMS FOR TREATMENT OF VENTILATOR ASSOCIATED PNEUMONIA (VAP) AND VENTILATOR ASSOCIATED TRACHEAL (VAT) BRONCHITIS

(71) Applicant: CARDEAS PHARMA CORPORATION, Seattle, WA (US)

(72) Inventor: Alan Bruce Montgomery, Medina, WA (US)

(73) Assignee: CARDEAS PHARMA CORPORATION, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/012,849

(22) Filed: Feb. 1, 2016

(65) Prior Publication Data

US 2016/0143931 A1    May 26, 2016

Related U.S. Application Data

(60) Division of application No. 14/480,514, filed on Sep. 8, 2014, which is a continuation-in-part of application No. 13/844,244, filed on Mar. 15, 2013, now Pat. No. 8,826,904, which is a continuation-in-part of application No. 13/548,115, filed on Jul. 12, 2012, now Pat. No. 8,603,439, said application No. 13/844,244 is a continuation-in-part of application No. PCT/US2012/046559, filed on Jul. 12, 2012.

(60) Provisional application No. 61/572,225, filed on Jul. 12, 2011.

(51) Int. Cl.

| A61K 31/7036 | (2006.01) |
|---|---|
| A61M 16/00 | (2006.01) |
| A61M 16/16 | (2006.01) |
| A61K 31/665 | (2006.01) |
| A61K 9/12 | (2006.01) |
| A61K 9/00 | (2006.01) |
| A61M 11/00 | (2006.01) |
| A61M 11/04 | (2006.01) |
| A61M 16/08 | (2006.01) |

(52) U.S. Cl.
CPC .......... *A61K 9/0078* (2013.01); *A61K 31/665* (2013.01); *A61K 31/7036* (2013.01); *A61M 11/005* (2013.01); *A61M 11/04* (2013.01); *A61M 16/0057* (2013.01); *A61M 16/0875* (2013.01); *A61M 16/16* (2013.01)

(58) Field of Classification Search
None
See application file for complete search history.

*Primary Examiner* — Robert A Wax
*Assistant Examiner* — Randeep Singh
(74) *Attorney, Agent, or Firm* — VLP Law Group LLC

(57) ABSTRACT

The present invention is antibiotic compositions, ventilator-based systems and methods relating to ventilator-associated pneumonia (VAP) and ventilator-associated tracheal (VAT) bronchitis. Antibiotic combinations of fosfomycin and an aminoglycoside, preferably amikacin, are administered via an inline nebulizer within the airway of the ventilator. Humidified conditions create an improved aerosol mist to treat VAP and VAT.

9 Claims, 5 Drawing Sheets

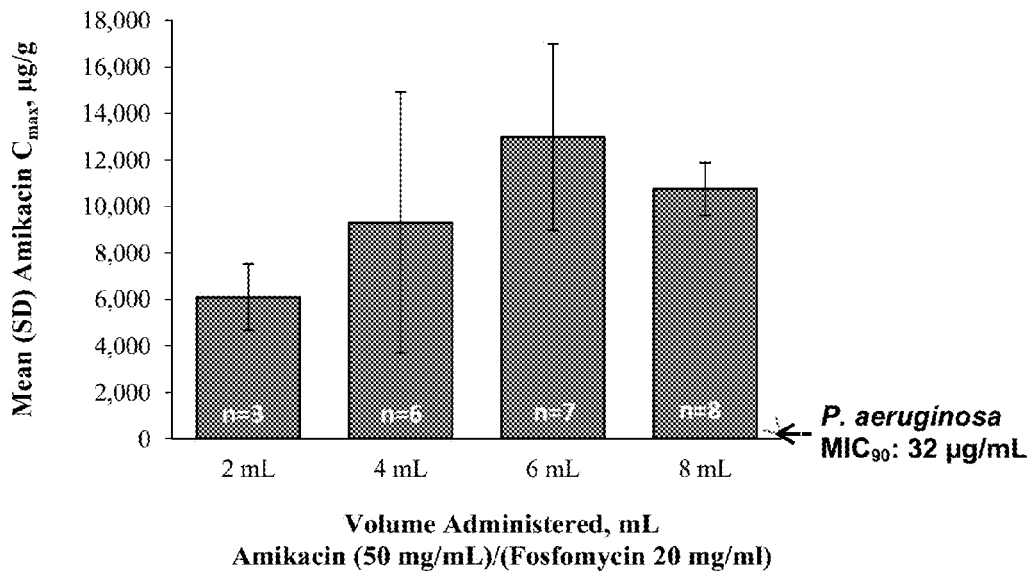
Figure 2. Tracheal Aspirates: Mean (SD) Amikacin $C_{max}$
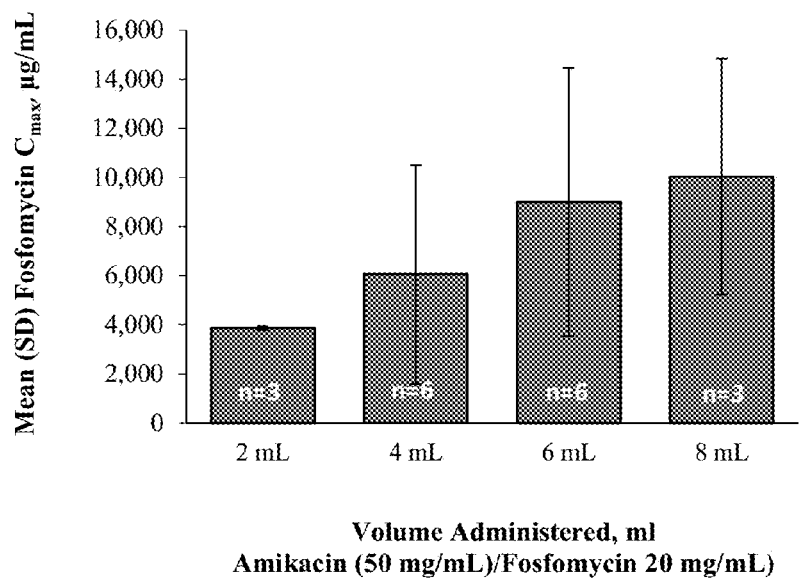
Figure 3. Tracheal Aspirates: Mean (SD) Fosfomycin $C_{max}$

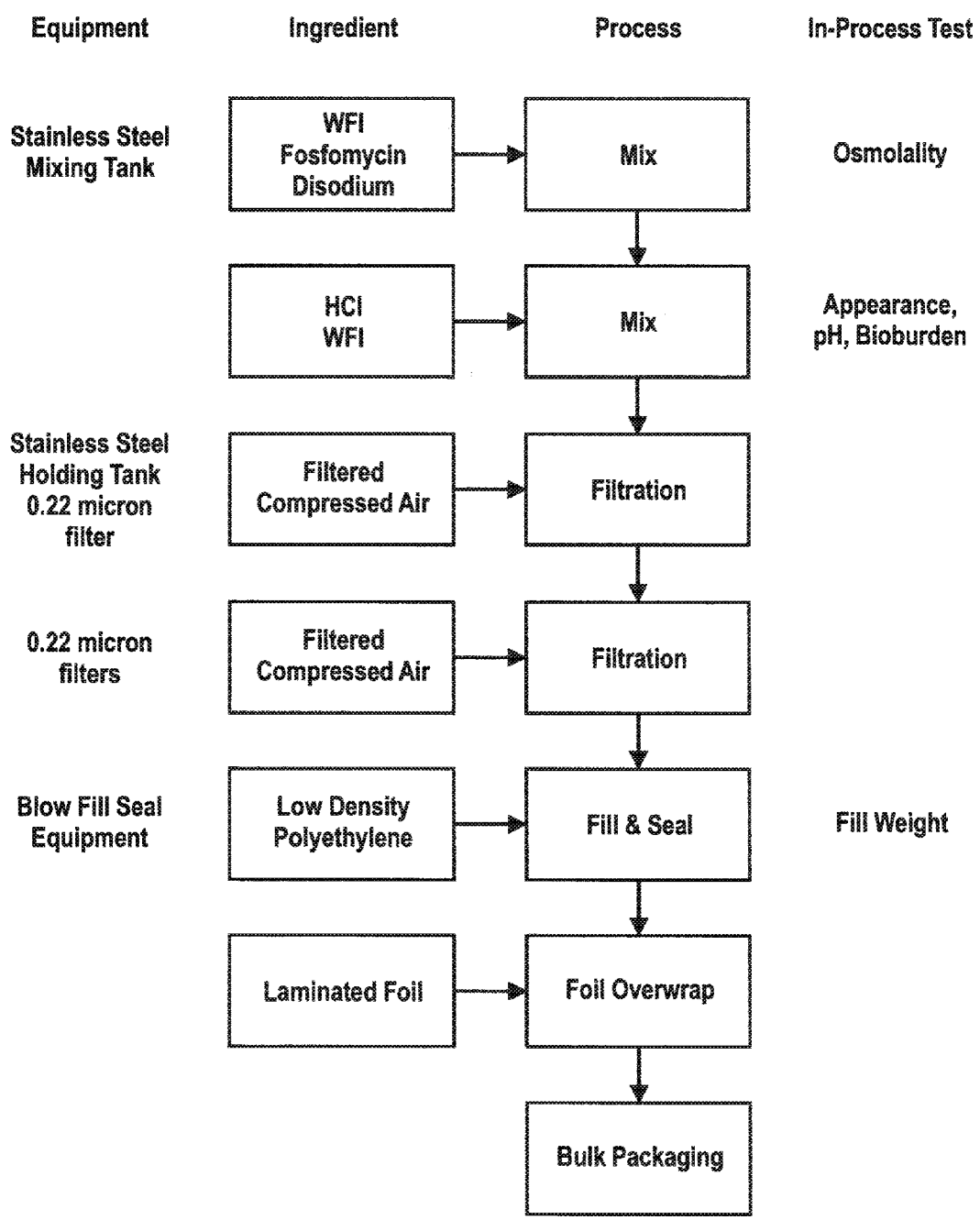
Figure 6 Fosfomycin Process Flow

FORMULATIONS OF AMINOGLYCOSIDE AND FOSFOMYCIN COMBINATIONS AND METHODS AND SYSTEMS FOR TREATMENT OF VENTILATOR ASSOCIATED PNEUMONIA (VAP) AND VENTILATOR ASSOCIATED TRACHEAL (VAT) BRONCHITIS

CROSS REFERENCE TO RELATED APPLICATIONS

This application is a divisional of U.S. application Ser. No. 14/480,514 which is a continuation-in-part of U.S. application Ser. No. 13/844,244 filed Mar. 15, 2013, now U.S. Pat. No. 8,826,904, which is a continuation-in-part of U.S. application Ser. No. 13/548,115 filed Jul. 12, 2012, now U.S. Pat. No. 8,603,439, which claims the benefit of U.S. Provisional Application No. 61/572,225 filed Jul. 12, 2011. U.S. Ser. No. 13/844,244 is a continuation-in-part of PCT/US12/46559 filed Jul. 12, 2012 which claims the benefit of U.S. Provisional Application No. 61/572,225 filed Jul. 12, 2011, which applications are incorporated herein by reference.

BACKGROUND

Considerable medical literature and clinical experience establish that ventilator associated pneumonia (VAP) is a feared and often fatal complication of mechanical ventilation. In the United States, over 250,000 patients per year are stricken with VAP or approximately 800 cases per million population. In Melbourne, the incidence in 2006 was reported as 6.2 cases per 1,000 ventilator days, similar to the rate in the United States. Sogaard O S et al., a binational cohort study of ventilator-associated pneumonia in Denmark and Australia, Scand J Infect Dis (2006), 38:256-264). The mortality of VAP averages 25%. Therefore, in patients with a poor prognosis, a VAP diagnosis is a life-threatening complication.

The onset and rapid progression to VAP usually occurs after 3-5 days of mechanical ventilation and starts with initial colonization of the airway with pathogenic bacteria. The initial colonization is followed by a purulent tracheobronchitis (also known as ventilator-associated tracheobronchitis (VAT)) which rapidly progresses to VAP. VAT is considered a precursor to VAP and is characterized as tracheobronchitis without new infiltrates on the chest radiograph (Nseir, Nosocomial tracheobronchitis Current Opinion in Infectious Diseases 2009, 22:148-153). However, not all VAT progresses to VAP, and not all VAP had a VAT precursor. In addition, pneumonia in a patient on a ventilator that was acquired in the hospital and or a nursing care facility prior to intubation and start of mechanical ventilation is often from the same highly pathogenic bacteria seen in VAP. Our use of the VAP term includes these patients as they have a similar course and prognosis of patients that develop pneumonia after initiation of mechanical ventilation.

In addition to patient mortality, VAP also prolongs ICU stays and is treated with high doses of intravenous antibiotics. However, the levels of antibiotics that can be achieved in the respiratory tract with intravenous administration are severely limited and are often lower than the effective concentrations needed to treat VAP. Moreover, the continuing emergence of drug-resistant organisms, particularly in hospital settings, makes treatment with intravenous antibiotics increasingly less effective. Specifically, the emergence of multidrug-resistant bacteria such as methicillin-resistant *Staphylococcus aureus* (MRSA), and highly virulent Gram-negative pathogens is increasing the morbidity of VAP.

Over the past twenty years, multiple investigator-sponsored trials have attempted to study aerosolized antibiotics to either treat or prevent VAP. (See Palmer et al. in Critical Care Medicine 2008, 36(7):2008-2013; Wood et al. in Pharmacotherapy 2002, 22(8):972-982; and Lu et al. in AJRCCM (Volume 184:106-115, 2011).) Meta analysis of these trials shows benefit in decreasing ventilators days and improving other outcomes. Recently, Palmer et al. supra performed a randomized blinded placebo-controlled trial to determine the impact of aerosolized antibiotics on outcomes in patients with VAT and/or VAP. Forty-three patients were randomized to receive aerosolized antibiotics or placebo for 14 days. Choice of the aerosolized antibiotics was based on Gram stain of the endotracheal aspirate. Vancomycin or gentamicin were used in patients with Gram-positive and Gram-negative microorganisms, respectively. Both antibiotics were used if both Gram-positive and Gram-negative microorganisms were present. Most of the 43 patients were also treated intravenously with systemic antibiotics. The authors found aerosolized antibiotics to be associated with significantly lower rates of VAP at the end of treatment, reduced usage of systemic antibiotics, and earlier weaning of patients from the ventilator—leading to shorter stays in the ICU.

Palmer et al. also showed the advantage of a cocktail of antibiotics, specifically gentamicin and vancomycin, that have Gram-negative and Gram-positive respective activity in treatment of VAP and VAT, as many patients are infected with both Gram-negative and Gram-positive bacteria. Interestingly, lower rates of antimicrobial resistance were also found in patients treated with aerosolized antibiotics, likely as suboptimal levels, commonly seen with intravenous administration, are known to promote the development of bacterial resistance.

The delivery system used by Palmer et al. was a small particle size jet nebulizer—no longer manufactured—that introduced an additional 6 L/m airflow into the airway. Such a nebulizer is incompatible with many modern ventilators because modern ventilators have sophisticated control, monitor, and feedback systems that carefully adjust airflow and pressures in the airway. A recent study by Lu et al. compared ceftazidime and amikacin, aerosol (n=23) vs. IV (n=17) in a small Phase 2 trial in established Gram-negative bacteria and VAP. After 8 days of antibiotic administration, aerosol and intravenous groups were similar in terms of successful treatment (70% vs 55%), treatment failure (15% vs 30%), and superinfection by other microorganisms (15% vs 15%). Antibiotic resistance was observed exclusively in the intravenous group. The authors concluded that aerosol antibiotics have similar efficacy to intravenous (IV) delivery and likely lead to lower rates of bacterial resistance.

The poor results of aerosol adjunctive therapy or primary antibiotic treatment in VAP is not surprising, because intravenous antibiotics penetrate poorly into the sputum. Aerosol antibiotics generally have a 100-fold higher sputum concentration than the maximum dose IV delivery and usually with one-tenth the systemic exposure. Aerosolized antibiotics are rapidly cleared from the respiratory tract, and their use can provide either very high concentrations in the lungs, which is desirable to control bacteria, or very low concentrations. This avoids long periods of sub-MIC antibiotic concentrations that lead to the development of resistance. However, to date, no aerosolized antibiotics for VAP or VAT have been approved by regulatory authorities.

A promising combination of Gram-negative and Gram-positive antibiotics for VAT and VAP would be the combination of an aminoglycoside and fosfomycin. (Baker U.S. Pat. No. 7,943,118 and MacCleod J Antimicrobial Chemotherapy 2009, 64:829-836.) In patients with cystic fibrosis (CF) and *Pseudomonas aeruginosa* (a Gram-negative bacteria) infections, an 80 mg fosfomycin/20 mg tobramycin dose delivered twice daily as an aerosol by a vibrating plate nebulizer (PARI® eFlow®) was effective in decreasing the bacterial burden of *P. aeruginosa*, and *Staphylococus aureus* over a 28-day treatment period (Trapnell et al., AJRCCM 185:171-178, 2012). Other aminoglycosides may also be synergistic with fosfomycin; Cai (J of Antimicrobial Chemotherapy 64 (2009) 563-566) reported that in both an in vitro and a systemically treated rat *pseudomonas* infection model, fosfomycin potentiated the efficacy of amikacin to an even greater extent than tobramycin.

In spontaneously breathing patients, the importance of a well-tolerated aerosol is also known. While mild cough can be tolerated in a patient on a ventilator, coughing increases the airway pressures, putting the patient at risk for barotrauma. It is well known that hyperosmolar solutions for nebulization can cause cough. In fact, a 7% hypertonic saline solution having an osmolality of 2411 Osm/kg is used to induce cough to obtain sputum specimens or to promote airway clearance in patients spontaneously breathing with lung disease. Lower osmolality solutions still cause cough. A formulation of fosfomycin/tobramycin with an osmolality of approximately 832 osm/kg when tested in CF patients caused noticeable coughing in 10 of 41 patients, while a placebo of normal saline (Osm/kg of 310) produced coughing in only 3 of 40 patients. Wheezing, a more several measure of bronchospasm, occurred in 5 of 41 patients compared to none in the placebo group. (AMJ Respir Crit Car Med 185:171-178, 2012.)

Therefore, although some combinations of antibiotics, including fosfomycin and aminoglycosides, have been used, combinations for VAP and VAT have not been approved, and several problems remain to be solved. First, ventilator circuits almost invariably include a humidifier to humidify the dry gas using sterile water coming from high pressure gas supplies prior to the gas entering the patient's airway. Humidification of the air leads to hygroscopic growth of the aerosol particles. Many particles grow to a large size and "rain out" in the endotracheal and ventilator tubing or, if delivered to the patient, deposit in the large airways rather than lungs. See Miller et al., Am J Respir Crit Care Med 168:1205-09 (2003). An endotracheal tube's internal diameter averages 7-8 mm, much smaller than the diameter of a typical trachea. The smaller diameter increases "rain out" of large >5 micron particles such that those aerosol particles never reach the patient. The efficiency penalty of leaving the humidification circuit on with use of jet nebulizer with an average particle size of approximately 5 microns (at the nebulizer prior to growth due to humidification) has been estimated as a loss of 50% of the aerosol. (Palmer et al. in Critical Care Medicine 1998:26:31-38.) To avoid this problem, the obvious resolution is to turn off the humidifier during aerosol antibiotic therapy, as was done in the treatment studies noted above (Palmer, Wood, Lu, Miller, supra). This is a successful approach but carries the finite risk of a health care worker neglecting to turn humidification back on. Accordingly, hospitals, critical care facilities, and regulatory agencies would most likely require specific warning devices to maintain humidification, because non-humidified gas causes drying of secretions, which makes recovery from pneumonia even more difficult. A method that allows continuous humidification is optimal and would increase patient safety and treatment efficacy.

Second, improved airway tolerance is needed for patients with VAT and VAP. In the recent study of Lu et al., patients commonly breathe out of sequence from the ventilator, likely caused by irritation from the therapeutic aerosol. Eschenbacher (Eschenbacher et al., Am Rev Respir Dis 1984, 129: 211-215) published that mild asthmatic patients will cough when exposed to an aerosol without a permeant anion (such as chloride) concentration greater than 20 meq/liter even if the aerosol is isotonic. Lu utilized sterile water to reconstitute the powdered antibiotics and did not use any saline that would provide a permeant anion in his formulation. Lu's approach was to heavily sedate the patient, which is not optimal.

Third, Eschenbacher (supra) tested a hypertonic saline solution of 1232 mOsm/liter in mild asthmatic patients and showed that cough and bronchospasm were common. Pretreatment with bronchodilators could prevent bronchospasm but could not prevent cough. As noted above, coughing in the ventilator is not desirable, as it can cause high airway pressures leading to pneumothorax or interfere with delivery of adequate ventilation. The osmolality of a fosfomycin/tobramycin combination currently being used in clinical studies of outpatient cystic fibrosis (CF) patients is approximately 832 mOsm/liter, far above the physiologic airway osmolality of approximately 310 mOsm/liter. The high osmolality is due to the low MW of fosfomcyin, coupled with the formulation of fosfomycin as a disodium salt. The disodium salt of fosfomycin has a solubility of 50 mg/mL of water; other salts including calcium are available, but have less solubility such that concentrated formulations are not practical. The high osmolality formulation is used so that each dose can be delivered in a 2 mL solution in a vibrating mesh nebulizer so treatment time for a CF outpatient is approximately 5 minutes. More dilute solutions would require longer administration times, which lead to poor compliance and potentially less efficacy. Higher osmotic concentrations have larger hygroscopic growth. Thus, if such formulations were used in a ventilator, a large amount of >5 micron particles would rain out in the tubing, and the remaining amount that was delivered would likely be irritating to the airways. A common adverse event of cough was reported in the phase 2 CF study. In fact the high dose (160 mg fosfomycin/40 mg tobramycin, same osmolality in a 4 mL solution) was very poorly tolerated in the CF study in spite of all the patients pretreated with a bronchodilator to prevent bronchospasm.

Fourth, the epidemiology of resistance and goals of therapy are very different in VAP and VAT compared to outpatient CF. Moreover, in the hospital setting, once bacterial resistance occurs, the spread of resistant bacteria between patients is rampant and epidemics are common. Furthermore, the risk of aminoglycoside-related toxicity from the cumulative long-term dose is serious because CF patients are treated chronically for years with tobramycin aerosols. See Baker et al., U.S. Pat. No. 7,943,118. In contrast, in VAT and in VAP, a patient is likely to receive only a single, two-week course of antibiotics. Therefore, when used to treat VAP or VAT, limiting the dose of an aminoglycoside in a combination product, and relying on fosfomycin to increase bacterial killing, risks the loss of efficacy of both drugs if a patient has bacteria that are fosfomycin resistant. For example, in contrast with high ratios of fosfomycin to tobramycin disclosed in Baker, et al., an optimal formulation in VAP and VAT would have enough of an aminoglycoside dose to be an independently effective antibiotic combination. However, this approach would only increase the osmolality of the formulation if the ratio of the formulation is held constant. The advantage of the fosfomycin would be to further enhance Gram negative killing, including biofilms (Cai, supra) and to also treat Gram positive bacteria, including methicillin resistant *Staphylococcus aureus* (MRSA). Another advantage of fosfomycin is that it reverses some of the sputum antagonism that limits the bioavailability of aminoglycosides (MacCleod, supra), (Mendelman Am Rev Respir Dis 1985, 132:761-5). Thus, even if the bacteria is fosfomycin resistant, there may be some clinical benefit to the combination by increasing the bioactive concentrations of the aminoglycoside.

One solution would be to dilute the formulations and increase the volume placed in the nebulizer for treatment. However, observation of a patient during therapy is likely to be standard protocol. ICU specialist nurses or respiratory therapists would likely be required to observe the patient during treatment adding additional costs to the therapy due to the prolonged administration time. Serious adverse events can occur during aerosol therapy, such as in Lu's study, where a patient had a cardiopulmonary arrest due to a clogged exhalation filter on the ventilator. An optimal formulation would have shorter delivery time than that of a dilute formula. Triggering the delivery during inspiration would extend treatment time but the time loss may be offset by improvement in the efficiency of delivery. Thus, a need for a treatment protocol exists wherein lower doses may be evaluated.

Accordingly, a need exists for antibiotic compositions, equipment, and treatment methods and systems to alleviate or prevent VAT and VAP despite the known challenges and the recognized risks.

SUMMARY OF THE INVENTION

The present invention is an improved formulation of an aminoglycoside, and specifically improved amikacin with fosfomycin in combinations, systems, and methods for the treatment, alleviation, and prevention of ventilator associated pneumonia (VAP) and ventilator associated tracheal (VAT) bronchitis. The antibiotic compositions of the invention include combinations of specifically formulated amikacin and fosfomycin, combined in a hypertonic solution having specific concentrations and ratios, predetermined concentrations of permeant ion designed to be tolerant upon inhalation, including specifically chloride ion (Cl-concentrating), pH ranges, particle sizes in an aerosol mist, and osmolality levels designed to further the therapeutic goals of the invention. These physical and chemical parameters are uniquely selected to enhance the bacteria static and bactericidal performance of the drug combinations in both ventilator-based and nebulizer-based modes of administration. Specifically, the ratios of amikacin to fosfomycin are greater than 1:1, greater than 9:5, greater than 2:1, and preferably greater than or equal to 2.5-2.6:1.0. The pH range is generally between about 4.4 and 7.5 and preferably between 6.9 and 7.4. The concentration of permeant and ion is greater than 30 equivalents per liter and, in some formulations, greater than 40 milliequivalents per liter. The osmolality is greater than 300-310 mOsm/Liter and less than about 800 mOsm/Liter and generally less than 1,000 mOsm/Liter. The concentration of the first and second antibiotic component is both individually and synergistically in combination, bactericidal, and preferably having a quantity greater than MIC 90 for a target organism. The aerosol can be formed from a solution containing any low molecular weight drug that requires high concentrations for efficacy, or cations or anions of such drugs having an osmolality that is higher than desired for tolerance upon aerosol administration. In certain embodiments described below, the antibiotic components may be either liquids, solids, or formulated as aerosols or dry powders and may be any physiologically compatible salt of the compositions described herein.

The first component of the antibiotic combination and composition is amikacin, a well-known and widely used aminoglycoside having activity against Gram-negative organisms. Although amikacin is not approved for aerosol use, it has been used in multiple VAP studies as regimen component that includes either standard IV drugs or ceftazidime aerosol. See Niederman, et al., NKTR-061 (Inhaled Amikacin) Reduces Intravenous Antibiotic Use in Intubated Mechanically Ventilated Patients During Treatment of Gram-Negative Pneumonia. from 27th International Symposium on Intensive Care and Emergency Medicine Brussels, Belgium. 27-30 Mar. 2007 Critical Care 2007, 11 (Suppl 2):P97,5, Lu Q, et al., Nebulized ceftazidime and amikacin in ventilator-associated pneumonia caused by *Pseudomonas aeruginosa* in AJRCCM Articles in Press. Published on Apr. 7, 2011 as doi:10.1164/rccm.201011-18940C). Systemic exposure is low with aerosolized amikacin and thus safer than intravenous administration in regards to renal toxicity. A data base of greater than 15,000 hospital pathogens was recently published and represents current resistance data after a generation of amikacin use Zhanel G G, et al., Antimicrobial susceptibility of 15,644 pathogens from Canadian Hospitals: results of the CANWARD 2007-2009 study. Diagnostic Microbiology and Infectious Disease 69 (2011) 291-306). The MIC 90 (The minimal inhibitory concentration of 90% of the isolates) was 32 µg/ml for *Pseudomonas*. In all other Gram negatives with the exception of *Stenotrophomonas maltophilia*, the MIC 90 was lower. The MIC 90 of *S. maltophilia* was >64 µg/ml. The limitations of amikacin are that its activity against MRSA is limited, and activity against Gram negative bacteria in biofilms is poor. Also, amikacin formulated for intravenous use is the sulphate of the amikacin base and is not ideal for inhalation therapy because sulphate is not a permeant anion. Accordingly, the amikacin base is formulated with chloride as the counter anion for tolerability and efficacy. See Examples 6 and 7 below.

The second antibiotic component of the drug formulation is fosfomycin, a broad spectrum phosphonic acid antibiotic that has both Gram-positive and Gram negative activity. Fosfomycin oral monotherapy is commonly used to treat uncomplicated urinary tract infections. Recently fosfomycin was proven to be safe and effective as an aerosol in combination with tobramycin in treating CF patients with *pseudomonas* infections. Trapnell B C et al., Fosfomycin/Tobramycin for Inhalation (FTI): Efficacy Results of a Phase 2 placebo-controlled Trial in Patients with Cystic Fibrosis and *Pseudomonas aeruginosa*. Poster 233 24th Annual North American Cystic Fibrosis Conference, Oct. 21-23, 2010, Baltimore, Md., Trapnell B C et al., Fosfomycin/Tobramycin for Inhalation (FTI): Safety Results of a Phase 2 placebo controlled Trial in Patients with Cystic Fibrosis and *Pseudomonas aeruginosa*. Poster 234 24th Annual North American Cystic Fibrosis Conference, Oct. 21-23, 2010, Baltimore, Md. In addition, fosfomycin was effective against MRSA coinfection in approximately one-third of treated patients. The antibiotic's efficacy with amikacin is superior to what is seen with tobramycin. Cai et al. reported that fosfomycin in vitro increased the activity in vitro of amikacin by a factor if 64, and in a rat biofilm *pseudomonas* infection model the combination of fosfomycin and amikacin improved efficacy compared to monotherapy of either component. Cai Y et al. Synergistic effects of aminoglycosides and fosfomycin on *Pseudomonas aeruginosa* in vitro and biofilm infections in a rat model. J of Antimicrobial Chemotherapy 64 (2009) 563-566. Fosfomycin is not used in North America as an IV antibiotic, and there is no recent data on fosfomycin MICs from MRSA. However, data from the 1980s reports an MIC 90 of 32 µg/ml. Alvarez S et al., In Vitro activity of Fosfomycin, Alone and in Combination, against Methicillin-Resistant *Staphylococcus aureus*. Antimicrobial Agents and Chemotherapy 28 (1985) 689-690). With little general use, one would expect similar values today, i.e., not showing development of substantial resistance.

In one embodiment, the combined formulation will be a neutral pH hypertonic solution of at least about 50 mg/mL of amikacin with chloride as the counter anion, and at least about 20 mg/mL of fosfomycin with at least 30 equil/L of chloride anion. The osmolality of this formulation will be approximately 700 mOsm/L, and with dilution from the humidification from the ventilator circuit, the final osmolality will be approximately 425 mOsm/L. Normal airway osmolality is 310 mOsm/L, and mildly hypertonic solutions are well tolerated by patients. The use of a permeant anion is to prevent cough in patients with mild asthma and is used in approved aerosol antibiotic formulations such as tobramycin solution for inhalation and aztreonam for inhalation. Eschenbacher W L, Alteration in Osmolarity of Inhaled Aerosols Cause Bronchoconstriction and Cough, but Absence of a Permeant Anion Causes Cough Alone. Am Rev Respir Dis (1984); 129:211-215.

The peak concentrations that one can achieve in the sputum can be predicted by estimating the mass of drug delivered to the lower airways in mg and multiplying by a factor of 30 to get an estimate of concentrations. For instance for TOBI, 36 mg is delivered to the lung and the sputum concentrations are approximately 1,000 μg/ml. For Cayston® (Aztreonam Lysine), 30 mg is delivered and the concentrations are approximately 750 μg/ml. VAP patients have much less sputum average likely less than 10 mL, than a patient with CF or bronchiectasis, that average over 100 mLs. Therefore, tracheal concentrations are typically 10 fold higher in VAP patients compared to sputum concentration in CF and bronchiectasis patients if the same amount of drug is delivered to the lung.

About 45 mg of amikacin and about 30 mg of fosfomycin are delivered to the lung if a 6 mL dose (50 mg amikacin and 20 mg fosfomycin in solution) is used in a nebulizer with an expected 15% delivery efficiency. The predicted concentrations of amikacin would be about 13,500 μg/ml, greater than 25 times the MIC 90 for most Gram negative organisms. The predicted peak concentrations of fosfomycin would be about 5400 μg/ml; again more than 25 times greater than the MIC 90 for *Staphylococcus aureus* based on the similar ratios of deposited drug (in mg) to sputum concentrations in μg/ml of 30 that is seen with tobramycin and aztreonam aerosols after correction for sputum volume differences between CF, bronchiectasis as compared to VAP. With the exception of pentamidine that has a prolonged half-life in the lung due to binding of the drug to surfactant in the alveolar space, the two other FDA-approved inhaled antibiotics, tobramycin and aztreonam, have an airway half-life of about 2 hours. Thus, dosing for aerosolized antibiotics is generally BID (twice daily) or TID (three times daily) because little therapeutic drug remains after 5 half-lives or ten hours. Systemic absorption of deposited drug is about 10%; thus, even with sputum concentrations on average 100-fold greater than what can be achieved with intravenous drug, the systemic exposure of aerosol antibiotics is on the order of 10% of a therapeutic intravenous dose.

Peak concentrations are not a perfect predictor of efficacy. In the case of amikacin, sputum is known to antagonize the bioavailability of amikacin and thus doses that achieve at least tenfold the MIC 90-fold higher are needed for efficacy. Mendelman et al., Aminoglycoside penetration, in activation, and efficacy in cystic fibrosis sputum. Am Rev Respir Dis (1984); 132:761-765). Efficacy is also known to be correlated with peak concentrations of aminoglycosides, making aerosol delivery with the high concentrations nearly ideal. In the case of fosfomycin, time above the MIC is more important than peak concentrations. The half-life of inhaled aerosol is on average approximately 1.5-2 hours, so a 5400 μg/ml initial dose would be at the MIC 90 of MRSA as early as eight half-lives or about 12 hours.

Twice daily dosing is preferred due to the rapid clearance of fosfomycin, and prior study data from aminoglycoside treatment. In a Phase 2 VAP study comparing once-a-day versus twice a day administration, aerosolized amikacin as adjunctive therapy to IV antibiotics, twice a day was superior in reducing the need for additional salvage antibiotics Niederman, et al. NKTR-061 (Inhaled Amikacin) Reduces Intravenous Antibiotic Use in Intubated Mechanically Ventilated Patients During Treatment of Gram-Negative Pneumonia. from 27th International Symposium on Intensive Care and Emergency Medicine Brussels, Belgium. 27-30 Mar. 2007, Critical Care 2007, 11 (Suppl 2):P97). Uniquely challenging bacterial infections subject to treatment by the compositions of the invention are organisms that are drug resistant, such as MRSA, and those harboring genes that confer bacterial resistance. In particular, genes encoding the carbapenemase enzymes. These beta lactamase enzymes confer resistance to beta lactam antibiotics by hydrolyzation of carbapenems. The New Dehli metallo-beta-lactamase-1 (NDM-1) is a class B metallo-beta-lactamase that has spread worldwide and is frequently associated with so-called "super bugs" due to the rapid spread and resistance to antibiotics conferred by the enzyme. Genes encoding NDM-1, or other carbapenemases, can be exchanged between organisms by a variety of methods including conjugation, plasmid exchange, and bacteriophage transduction. The genes can be incorporated into the bacterial chromosome or borne by a plasmid. Treatment by the methods and compositions of the invention may follow identification of a carbapenemase in a bacterial isolate or by any standard methodology that establishes infection of a patient with a bacteria exhibiting antibiotic resistance. Accordingly, the methods of the invention include administering the compositions and utilizing the methods described herein in combination with bacterial diagnostics and in response to identification of a resistant organism in a patient.

An ideal aerosol delivery system for existing mechanical ventilators would have the following parameters: the system would be compatible with all ventilator models made of disposable components; capable of creating small particle aerosol size to prevent rain out in the endotracheal tube; and capable of rapid delivery of therapeutic quantities of antibiotic without creating additional airflow to trigger ventilator alarm or control systems. A nebulizer with these parameters, the investigational PARI eFlow inline nebulizer, yields the data disclosed herein. By vibrating a laser-drilled, thin stainless steel membrane, a small nearly uniform particle aerosol is created for drug delivery. This technology has been proven in the handheld Altera® device recently approved to deliver aztreonam for inhalation in cystic fibrosis patients with chronic endobronchial *pseudomonas* infections. A similar membrane, modified by a smaller hole size and located in a unit that is placed inline with a ventilator inspiratory tubing is preferred. The design is unique with the membrane in the middle of the tubing, with the inspiratory flow freely moving around the membrane to entrain the aerosol as it is created (See FIG. 1). The nebulizer will be run continuously, and the estimated lung deposition is 15%. Bias flow, if a feature on the ventilator, will be adjusted to less than 5 liters/minute to prevent excess flushing of the drug during exhalation.

FIG. 1 is a schematic of a system of the present invention comprised of a complete airway including a ventilator 1, inspiratory 2 and expiratory limbs 3, a humidifier 4, an inline nebulizer 5, and a fixture 6 for operably connecting the system to a patient. The position of the humidifier 4 is preferably proximate to the inline nebulizer 5, and the nebulizer 5 is most proximate to the patient. The humidifier 4 and the nebulizer 5 are both joined to the airway of the ventilator by a fixture that is sealed at each point of attachment to the inspiratory limb 2 such that additional air is not introduced into the inspiratory limb 2 during inspiration by the patient. The antibacterial composition yielding a hypertonic solution is introduced into the nebulizer 5 for administration to the patient. Unlike drug administration protocols provided in the medical literature, the humidifier 4 is affirmatively activated during operation of the nebulizer 5 to achieve the method for reducing the osmolality of the hypertonic solution as described above. As noted above, the humidifier 4 and/or the nebulizer may be activated by a controller or program operating the ventilator 1, by patient inspiration, or may be continuous during administration of the drug combination(s).

Because humidification does not need to be turned off during delivery, the small particles grow to an average size of about 3.2 microns after humidification, leading to excellent peripheral deposition. The nebulizer is designed to be in line for the entire treatment course. The electronic control unit, the size of a cell phone, is plugged into the wall outlet with a cord that attaches to the nebulizer 5. The nebulizer 5 would be inserted near the distal end of the inspiratory tubing to work with any positive-pressure ventilator 1. Unlike a jet aerosol device, the system of FIG. 1 would not introduce any additional air and would avoid hyperinflation or barotrauma in a patient. The disposable drug/device components eliminate the cost of cleaning, and the one-time placement and ventilation of the nebulizer 5 in the system reduces the risk of bacterial contamination of a nebulizer, a known source of nosocomial infection. Leaving the nebulizer in place between treatments minimizes the opening of the ventilator circuit to the environments, a well-known risk for superinfection. In addition, a single patient use prevents any risk of patient-to-patient transmission of resistant bacteria. Drug delivery time would likely be approximately 20 minutes, twice a day.

In the methods of the present invention, a combination of amikacin and fosfomycin is administered from solution at a ratio of amikacin to fosfomycin greater than 1.1, greater than 9:5, greater than 2:1, and preferably greater than or equal to 2.5-2.6:1. The amikacin is formulated as amikacin chloride as described in Examples 6 and 7 below. The combination of antibiotics is dissolved in a hypertonic solution as described herein and is used to create an aerosol mist having a mean particle size less than five microns and an osmolality less than 1000 mOsm/L. The combination is preferably delivered by placing each in a reservoir in the inline nebulizer located within the airway of a mechanical ventilator. Alternatively, either component may be delivered by attaching a drug reservoir such as a dry powder container at a point where inspiration by the patient or movement of air in the ventilator airway advances drug composition to the patient. The two-part amikacin:fosfomycin formula ideally has a near neutral pH resulting from balancing the quantity, concentration, pH, and formulation of the individual components.

Preferably, the nebulizer is sealed in the airway to prevent additional airflow from being introduced and to permit a combination of the aerosol mist of the antibiotic formulation with humidified air generated by the ventilator system. In the system described herein, movement of air through the pathway of the ventilator combines humidified air and the aerosol mist containing the antibiotic formulation. Movement of air containing the aerosolized drug combination may be triggered by patient inspiration or as part of a continuous or programmed delivery protocol such that the nebulizer is in intermittent or continuous operation during the administration of the antibiotic combination. In each case, the formation of the aerosol is maintained by the apparatus for a duration adequate to deliver bacteriostatic or bactericidal amounts of the antibiotic combination to the lung of the patient.

The calculation of the total antibiotic delivery may be achieved by the quantity or concentration of the antibiotic, bactericidal dose, such as the MIC 90 for any identified organism, or it may be determined through clinical observation of the organism. As described in connection with FIG. 1 below, the ventilator system typically has an airway that extends from the pressure-generating components of the ventilator through the airway and into the wye fixture that terminates at the patient. The inline nebulizer may be placed at any point in the airway between the positive pressure-generating mechanics of the ventilator and the patient; however, the placement of the nebulizer proximate to the patient near the ventilator wye piece is preferred. The nebulizer and the humidification apparatus of the ventilator should be oriented so that the humidified air causes hygroscopic growth of the individual particles in the aerosol mist. As noted elsewhere herein, the advantageous expansion of the aerosol mist particles from an initial size to an enlarged size, caused by the humidification effect on the radius of each particle, will dictate the location of the nebulizer and the humidification apparatus. The combination of the humidified air and the antibiotic solution mist must also achieve reduction in the osmolality as described herein.

In practice, a patient is connected to a ventilator for breathing assistance and the ventilator system is adjusted to provide for a continuous and controlled airflow based on known physiological parameters. The antibiotic composition of the invention is introduced into a reservoir in the nebulizer and is stored therein until delivery. To administer the antibiotic combination of the present invention, the inline nebulizer is connected to the airway of the ventilator and activated to create the aerosol mist. Upon delivery, the nebulizer generates the aerosol mist from a vibrating apparatus disposed therein, typically a vibrating mesh or membrane that has numerous apertures formed therein to produce particles of a defined size from solution. The humidification generator is activated and maintained in operation during each delivery of the aerosol mist formed from the hypertonic solution such that the osmolar load is reduced. Thus, the advantage of an inline nebulizer as described herein is to permit the humidified air in the ventilation airway to pass through the nebulizer and to combine with the aerosolized portion of the hypertonic antibiotic combination solution.

Although the embodiment for treatment of VAP and VAT is described herein in the context of a treatment that occurs while a patient is connected to a mechanical ventilator system, the compositions of the present invention are suitable for administration to a patient who has been removed from a mechanical ventilator but continues to suffer a bacterial infection, typically as a result of the aftermath of a diagnosed VAP or VAT condition. In such cases, the antibiotic composition of the present invention can be delivered through an ordinary nebulizer as in the case of antibiotics delivered to patients suffering from cystic fibrosis. In such circumstances, the total composition of the administered antibiotic, the formulation parameters, and all other characteristics of a bactericidal treatment regimen are maintained.

DESCRIPTION OF THE FIGURES

FIG. 2 is tracheal aspirates mean (SD) amikacin Cmax.

FIG. 3 is tracheal aspirates mean (SD) fosfomycin.

FIG. 6 is a flow diagram of the manufacturing steps of the fosfomycin solution.

DETAILED DESCRIPTION OF THE INVENTION

Figure 1:
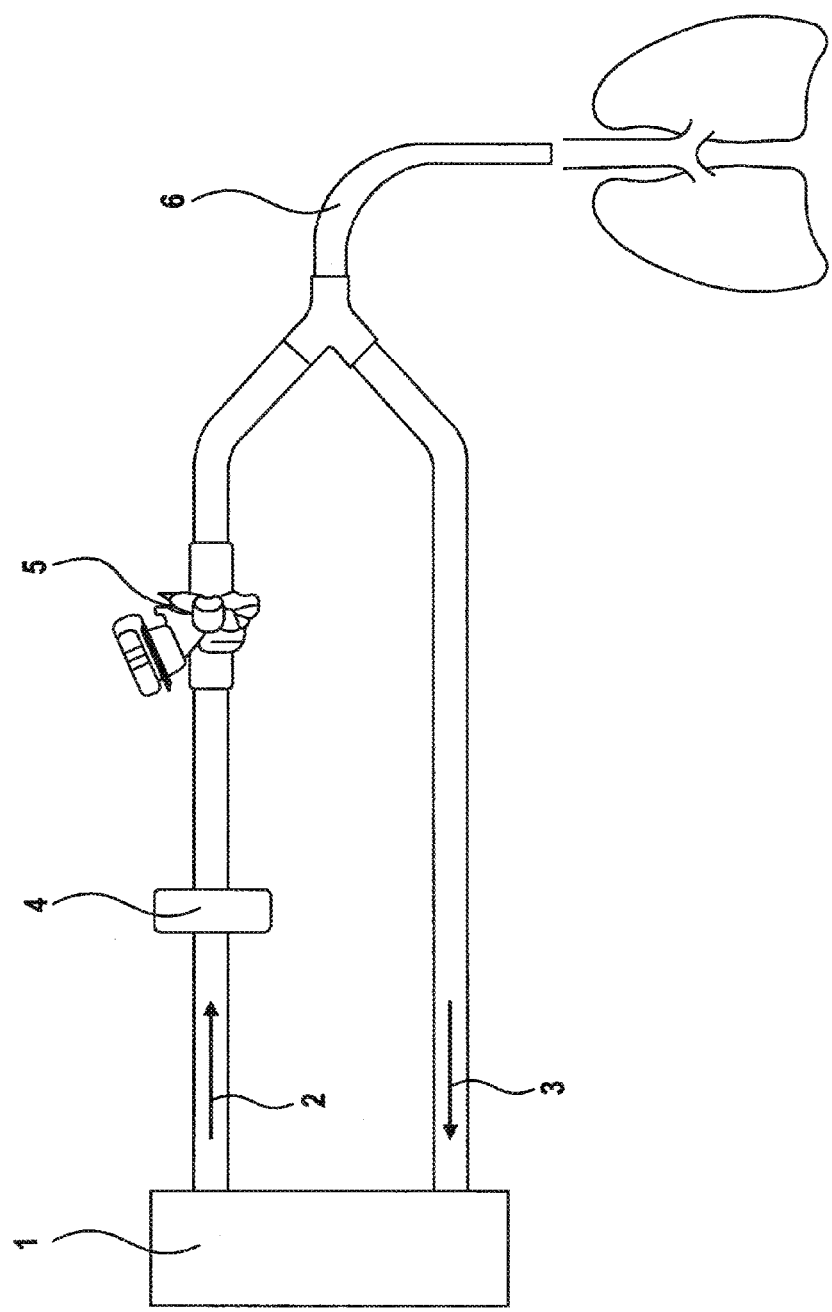
FIG. 1 is a schematic of a ventilator and inline nebulizer configured to deliver the compositions and perform the methods of the present invention.

Amikacin is a preferred aminoglycoside in the ICUs and in ventilator patients due to its better activity against *Acinetobacter baumannii* bacteria than tobramycin. In aerosol studies, a nebulizer dose of 400 mg amikacin led to mean sputum concentrations of 11,900 µg/ml with a wide variability with median <6400 µg/ml. Niederman et al, BAY 41-6551 Inhaled Amikacin achieves bactericidal tracheal aspirate concentrations in mechanically ventilated patients with Gram-negative pneumonia (Intensive Care Medicine 38:263-271, 2012) A Pharmacokinetic Study ATS 2010 New Orleans, La.). The vibrating plate nebulizer used in this study triggered only on inspiration and delivery time of a 2.7 mL formulation averaged 50 minutes. If run continuously, the PARI vibrating plate nebulizer has about 15% delivery efficiency and can deliver a 6 mL dose in 12 minutes. Hahn et al In vitro assessment of a novel nebulizer for mechanically ventilated patients based on the eFlow® technology, ISAM 2009, Monterey Calif. In the phase 2 CF fosfomycin/tobramycin study, the nebulizer dose of tobramycin was only 20 mg, with estimated 5 mg delivered to the lung. This illustrates the synergy seen with a combination of fosfomycin and an aminoglycoside. However, relying on synergy is not appropriate in VAP patients where the bacteria may be resistant to fosfomycin and is a life threatening condition.

The doses of aminoglycosides at first examination may seem excessive; however, sputum macromolecules bind aminoglycosides, so up to 90% of aminoglycoside is bound and therefore inactive. Therefore, with aerosol aminoglycoside monotherapy, a sputum concentration that is a least tenfold higher than the MIC 90 is considered necessary, and higher-fold concentrations, up to 25-fold may provide increased bacterial killing (Mendelman Am Rev Rispir Dis 1985; 132:761-5). Fosfomycin interferes with the sputum antagonism, (MacCleod, supra), thus even if the bacteria are fosfomycin-resistant, there may be some clinical benefit to the combination by increasing the bioactive concentrations of the aminoglycoside.

The optimally effective dose of fosfomycin is likely at least 15 mg delivered to the lung, with nebulizer doses ranging from 50 to 200 mg depending on nebulizer efficiency. This is based from the successful phase 2 CF trial (Trapnell et al., supra), which showed decreased bacterial density of both *pseudomonas* and *Staphylococcus aureus* in the subset of patients who were co-infected, with approximately 20 mg delivered to the lung. In this trial, an estimated 40 mg delivered dose of fosfomycin was more efficacious in killing *staphylococcus* than the estimated 20 mg dose, showing that a higher dose may be better. The most soluble fosfomycin salt is the disodium salt and is preferable although other salts are possible—such as calcium and tromethamine.

The recent development of vibrating plate nebulizers, particularly one by PARI, enables particle sizes less than 5 microns. See WO 2005/048982A2. Membranes having a plurality of small apertures therein can produce mean particle sizes less than 5 microns and in the range of 3.5 microns. This is accomplished by making the porous holes smaller during the laser drilling process. Other vibrating plate membranes by PARI have a 4.5 micron average size particle as does the vibrating plate nebulizer introduced by Aerogen/Nektar. Similarly, there are small particle jet nebulizers that can produce 2 3 micron size particles. Current ultrasonic nebulizers produce an average particle size of 5 microns using a 2.7 Mhz driving frequency. Ultrasonic nebulizers can create smaller particles by increasing the frequency of the ultrasonic generator. No high frequency (2.3 Mhz) nebulizers are currently commercially available in the United States or Europe at this time, but would have a 2-3 micron particle size. In addition, ultrasonic nebulizers heat the nebulizer solution and this may lead to drug degradation during therapy, for this reason, their use has fallen out of favor.

The present invention includes the use of humidification as a technique to improve the tolerability of hypertonic solutions delivered as an aerosol. The creation of an aerosol with a small particle size from a hypertonic solution can produce a composition of small particles that carry a desirable therapeutic dose but are poorly tolerated due to a high osmolality, i.e., on the order of threefold or greater of normal osmolality, (e.g., ≥930 mOsm/kg). Adding humidification to the aerosol yields an aerosol composition that has a reduced osmolality and is preferably close to isotonic or less than twofold normal osmolality (e.g., <620 mOsm/kg). The humidification is created by an inline humidifier to decrease the osmolality to a range from greater than threefold to less than twofold normal osmolality and may vary depending on the nature of the original hypertonic solution. The particle size of non-humidified aerosol such as the hygroscopic growth of a 4 micron particle may lead to much more dilution than growth of sub 3 micron particle. In such hypertonic solutions, the permanent ion in solution is preferably greater than 40 mequil/L. The humidification can be applied to aerosols formed from a variety of hypertonic solutions where paired tolerability is desired. Examples include any small molecular weight drugs that require high concentrations for efficacy, or compounds that are salts with multiple anions or cations that create a high osmolar load in solution.

In the aspect of the invention below, aminoglycoside/fosfomycin combinations are hypertonic on administration but close to isotonic upon delivery by the advantage of increased humidification compared to ambient air. For instance, if the particle size grows on average from 3.5 to 4.5 microns, the dilution is a function of the cube of the radius or 4.91/11.3. Therefore, the use of small particle aerosol with subsequent hygroscopic growth due to humidification would substantially reduce the osmotic load on the lung. With a larger initial particle size, the effect would be similar. For example, the growth from a 5 to 6 micron particle would lead to a dilution of 15.6/27. If particles are allowed to grow much larger than 5 microns, tolerability is not the primary issue, as little will be deposited in the airways due to "rain out" in the ventilator and endotracheal tubing. This was shown in the seminal studies by Palmer (supra) on the deleterious effect of humidification on total drug delivery. These studies mostly utilized jet nebulizers that have an average of 4-5 micron particles prior to growth due to humidification. The hygroscopic growth was responsible for rain out and less drug delivered to the airways. For instance, applying the ratio of 4.91/11.3, if a hypertonic solution is used with a nebulizer that has a 3.5 micron average particle, an osmolality of up to 710 would become, on average, isotonic. Slightly hypertonic formulations can be tolerated by the lung, and it is likely a formulation with an osmolality of up to 800 would be well tolerated by applying the humidification technique described herein.

The PARI inline nebulizer designed for ventilator use can be outfitted with a small pore membrane, has a current volume capacity of 10 mL, and has a rate of delivery of 0.5-0.6 ml/minute. Although it is currently not configured for triggering on inspiration, a nebulizer may be so configured when operably connected to the control system of the ventilator. Particle size would be estimated at 3.2 microns. A formulation of 10 mL, with 100 to 300 mg fosfomycin and 300 to 600 mg of amikacin at the 15% efficiency rate would provide adequate killing for *Staphylococcus aureus* and *Pseudomonas*. An ideal formulation would contain at least 20 meq/l of chloride anion after dilution. The estimated osmolality of a solution of 50 mg/mL amikacin and 20 mg/mL of fosfomycin, with chloride anion, adjusted to a pH between 4.5 and 7.5 is approximately 750-850 osm/L. If diluted by humidification, this would likely be close to the isotonic range when deposited in the airways. To vary the delivered dose, a smaller or larger volume could be used, or alternatively or in combination, trigger delivery on inspiration phase of breathing to increase the deposition amount.

Example #1

Preparation of Fosfomycin/Amikacin Solution for Aerosolization

A solution having a ratio of amikacin to fosfomycin of equal to or greater than 2.5-2.6:1 is prepared as follows: Fosfomycin disodium (12.90 g, 10.00 g free acid) was dissolved in 250 mL of water and the pH was adjusted to 7.41 by the dropwise addition of 4.5 N HCl (estimated 1 mL). 25 gm Amikacin base was added to the resulting solution. The pH of the solution was adjusted to 7.60 by the addition of 4.5 N HCl (total amount of 4.5 N HCl was 1.7 mL). The solution was diluted to 500 mL with water and filtered through a 0.2 μm Nalge Nunc 167-0020 membrane filter for sterility. The chloride content can be calculated by using 1.7 mL of 4.5 N HCl in 50 L total for a total 306 mg chloride. As 1 mEq Cl=35.5 mg in 1 L then in 50 mL 1 mEq Cl=1.775 mg. Therefore, 306 mg/1.775 mg=172.4 mEq/L.

The osmolality of this formulation was measured at 592 mOsm/kg, which is above the normal physiologic value of 310 mOsm.

Example #2

Reduction of the Osmolality of the Solution by Humidification

A solution having a fosfomycin/amikacin ratio of 2.5-2.6-1 amikacin to fosfomycin was prepared as above. Using an inline electronic vibrating late nebulizer (PARI, Starnberg G R), the formulation was nebulized in dry (4%) and humid (100%) humidity. The mean particle size, as measured by Malvern X laser particle sizer, was 2.9 μm under dry conditions, increasing to 3.2 μm under 100% humidity.

Since the volume of sphere is function of the third power of the radius, the following equation yields the dilution factor:

$$\frac{1.45 \times 1.45 \times 1.45}{1.6 \times 1.6 \times 1.6} = 0.75$$

Thus, the formulation on average is diluted by a factor of 0.75, indicating the delivered formulation has an osmolality of 592×0.75=444 mOsm/Kg.

Example #3

Randomized, Double-Blind, Placebo-Controlled, Dose-Escalation Phase 1 b Study of Aerosolized Amikacin and Fosfomycin Delivered Via the PARI Investigational eFlow® Inline Nebulizer System in Mechanically Ventilated Patients A dry powder fosfomycin, liquid amikacin solution can be prepared by use of 200 mg neat dry powder disodium fosfomycin filled in a glass vial or two-part dry liquid syringe. In either a separate syringe, blow fill seal container, or a two-part syringe, 500 mg of amikacin base dissolved in 10 mL of sterile water, with the pH adjusted to a range of 4.5 to 7.5 with HCl. The two components are then mixed together giving a solution with 20 mg/mL fosfomycin, 50 mg/ML amikacin. The osmolality of the solution would be approximately 600 mOsm/Kg, but could vary up to 10% depending on the amount of HCl used to adjust the pH of the amikacin solution. Also by employing the chlorine counter anion with the amikacin base, the sulfate salt of amikacin is not used.

A treatment regimen was designed to control safety, efficiency, tolerability and to further elucidate systemic and tracheal aspirate pharmacokinetics of nebulized amikacin/fosfomycin in patients with a clinical diagnosis of VAP following delivery of 2 mL, 4 mL, 6 mL, 8 mL, and 10 mL and doses via the PARI Investigational eFlow® Inline Nebulizer System in mechanically ventilated patients.

Adult patients having a clinical diagnosis of VAP, with a Gram-positive or Gram-negative organism in a tracheal aspirate sample were expected to be on mechanical ventilation for ≥3 days.

Each adult patient received 3 escalating doses of a mixture of 50 mg/mL amikacin and 20 mg/mL fosfomycin, with doses separated by 24±2 hours (Table 1). On Day 3, patients received 2 blinded, randomized treatments (amikacin/fosfomycin and volume-matched placebo [0.9% normal saline]), separated by 2 hours.

All treatments were administered with a single patient, multi-treatment nebulizer (Investigational eFlow® Inline Nebulizer System; PARI Pharma GMBH, Starnberg, Germany), positioned in the inspiratory tubing between the ventilator and the patient. The nebulizer remained inline until all treatments were delivered. As documented herein, the nebulizer has a vibrating perforated membrane and generates an aerosol with small droplets and narrow size distribution, which is optimal for deposition in the lower airways.

Concentrations of amikacin and fosfomycin were measured in tracheal aspirate and plasma samples obtained during the 24 hours after each dose, and the maximum concentration ($C_{max}$) was determined. Adverse events were assessed from the first dose until 24 hours after the last dose was received.

TABLE 1

Study Dosing Schedule

| Cohort # | Dose of Amikacin (50 mg/mL)/Fosfomycin (20 mg/mL) | | | | | |
|---|---|---|---|---|---|---|
| (Patient #) | 2 mL | 4 mL | 6 mL | 8 mL | 10 mL | 12 mL |
| 1 (1-3) | X | X | X[a] | | | |
| 2 (4-6) | | X | X | X[a] | | |
| 3 (7-9) | | | X | X | X[a] | |

Each patient received 3 treatments of amikacin/fosfomycin, with treatments separated by 24 ± 2 hours.
[a]On Day 3, patients received blinded, randomized treatment with amikacin/fosfomycin and with volume-matched placebo, with the 2 treatments separated by 2 hours.

TABLE 2

Bacteria Cultured from Tracheal Aspirates

| Bacterial Isolates | Number of Patients with Isolates[a] (N = 7) |
|---|---|
| Staphylococcus aureus | 3 |
| Citrobacter koseri | 1 |
| Enterobacter cloacae | 1 |
| Escherichia coli | 1 |
| Haemophilus influenzae | 1 |
| Proteus mirabilis | 1 |
| Serratia marcescens | 1 |

[a]Each patient had 1-2 different bacteria cultured from their tracheal aspirate.

TABLE 3

Concomitant Treatment with Intravenous Antibiotics

| Antibiotic Treatment | Number of Patients Treated[a] (N = 7) |
|---|---|
| Ciprofloxacin | 6 |
| Piperacillin/tazobactam | 6 |
| Vancomycin | 4 |
| Cefepime | 1 |
| Cefazolin | 2 |
| Ceftriaxone | 2 |
| Erythromycin | 2 |
| Gentamicin | 2 |
| Flucloxacillin | 1 |
| Meropenem | 1 |
| Moxifloxacin | 1 |

[a]Each patient received concomitant treatment with 3-5 intravenous antibiotics.

In tracheal aspirate samples obtained from each patient after each dose of amikacin/fosfomycin solution for nebulization. Each amikacin Cmax value was ≥89 fold higher than the minimum inhibitory concentration for 90% ($MIC_{90}$; 32 μg/ml) of 1477 Pseudomonas aeruginosa isolates described in a recently published isolate collection. Zhanel et al., Diagn Microbiol Infect Dis 2011, 69:291.

Mean amikacin Cmax after the 6 mL dose was ≥406-fold higher than the MIC 90 for P. aeruginosa (FIG. 2). Each fosfomycin Cmax value was ≥54-fold higher than the published MIC 90 value for 148 isolates of methicillin-resistant Staphylococcus aureus (MRSA; 32 μg/ml). Mean fosfomycin Cmax after the 6 mL dose was ≥281-fold higher than the MIC 90 for MRSA (FIG. 3). Six hours after dosing, all fosfomycin tracheal aspirate concentrations remained ≥2.2-fold above the MIC 90 for MRSA. Plasma concentrations were >2000-fold lower than concentrations in tracheal aspirates: The highest observed amikacin plasma concentration was 1.4 μg/mL; this is less than the recommended peak concentration (35 μg/mL) after a systemic dose. The highest observed fosfomycin plasma concentration was 0.8 μg/ml. No adverse event was considered by the clinical investigator related to study-drug treatment. No changes in oxygen saturation or peak airways pressures were noted in response to study drug. All patients were alive 28 days after completing the study. High tracheal aspirate concentrations of amikacin and fosfomycin were achieved in mechanically ventilated patients with VAP after aerosolized administration of amikacin/fosfomycin solution for nebulization with an inline nebulizer system. Systemic exposures to amikacin and fosfomycin were much lower than tracheal aspirate levels. Amikacin/fosfomycin solution for nebulization was well tolerated.

The combination antibiotic amikacin/fosfomycin (50 mg/mL amikacin and 20 mg/mL fosfomycin) formulation was delivered via the PARI Investigational eFlow® Inline Nebulizer System in mechanically ventilated patients. A placebo: 0.9% normal saline, having a volume matched to the antibiotic dosing schedule was delivered via the PARI Investigational eFlow® Inline Nebulizer System in mechanically ventilated patients.

The eFlow® Inline Nebulizer System was positioned in the inspiratory tubing between the Puritan Bennett 840 Ventilator and the patient. Once in place, the nebulizer remained inline until all study-drug doses were delivered. Humidification continued during the nebulization of the formulation and the delivery of the entire dose.

Patients are male or female between 18 years and 80 years of age with clinical diagnosis of VAP or VAT, a Gram-positive or Gram-negative bacteria on Gram stain of the tracheal aspirate and were expected to be on mechanical ventilation for at least three days.

These results support further clinical trials of amikacin/fosfomycin solution for nebulization in mechanically ventilated patients with VAP or VAT.

These results demonstrate that high sputum concentrations of amikacin and fosfomycin were achieved in mechanically ventilated patients with VAT or VAP after aerosolized administration with an inline nebulizer system.

Example #4

Clinical Study for VAT/VAP

A GLP (Good Laboratory Practice) study was performed using 24 beagle dogs allocated to four dose groups (three males and three females per group) and exposed to aerosol generated with the PARI Investigational eFlow® Inline Nebulizer System using a closed-faced mask fitted with a mouth tube. The aerosols contained either control (water for injection) in Group 1 or a combined formulation containing 50 mg/mL amikacin and 20 mg/mL fosfomycin pH adjusted with HCl for Groups 2 to 4. Aerosol concentrations were determined on Days 1 and 7. The treatment period was for seven days with termination of the dogs on Day 8. The average daily achieved dose of amikacin/fosfomycin for each group was 32.1:12.4 mg/kg/day (a 2.59:1 ratio) (Group 2); 63.0:24.7 mg/kg/day (92.55:1 ratio) (Group 3); and 116.8:47.5 mg/kg/day (92.46:1 ratio) (Group 4). The highest estimated pulmonary dose was 29.2 mg/kg/day amikacin and 11.9 mg/kg/day fosfomycin. The particle size distribution (MMAD [Mass Median Diameter]) based on analytical methods was determined to be respirable averaging 2.80 µm (GSD=1.778) for amikacin and 2.75 µm (GSD=1.670) for fosfomycin.

The aerosol was well tolerated by all dogs. There were no treatment-related adverse effects based on clinical observations, body weights, food consumption, ophthalmoscopy, or electrocardiography. Any changes to clinical pathology values observed were attributed to normal animal variation. No treatment-related abnormalities were observed on necropsy. No treatment-related adverse findings were observed upon histologic evaluation of tissues.

Toxicokinetic parameters were estimated using WinNonlin pharmacokinetic software version 5.2.1 (Pharsight Corp.). A non-compartmental approach consistent with the extravascular route of administration was used for parameter estimation. All parameters were generated from individual amikacin and fosfomycin concentrations in plasma from Days 1 and 7. Plasma amikacin and fosfomycin concentration vs. time profiles were consistent with the inhalation dose route whereby a post-dose absorption phase was followed by a biphasic bi-phasic decline in plasma concentrations. Systemic exposure to both amikacin and fosfomycin was generally comparable between males and females and there was no clear indication of accumulation following repeat dosing. The peak plasma levels (Cmax) for the high dose level on Day 7 ranged from 13.2 to 39.3 µg/ml for amikacin and 8.7 to 28.73 µg/ml for fosfomycin.

Based on the results of the study, significant exposure occurred following aerosol exposure to beagle dogs with no adverse effects observed over the 7-day treatment period. The NOAEL was considered to be 116.8 amikacin and 47.5 fosfomycin mg/kg/day delivered as a combination antibiotic aerosol. This is approximately 30-fold the estimated exposure to humans.

Example #5

Synergism of the Amikacin and Fosfomycin Combination Against Resistant, Gram-Negative Pathogens Sixty-two amikacin-resistant strains were selected from a worldwide antimicrobial surveillance collection (SENTRY), which contains 35,000 organisms from six continents (56/62 organisms collected in 2011). The 62 isolates of *Acinetobacter baumannii*, *Pseudomonas aeruginosa*, and *Klebsiella pneumoniae* had an amikacin minimum inhibitory concentration (MIC) of >32 µg/ml µg/mL (Clinical and Laboratory Standards Institute [CLSI]: intermediate or resistant; European Committee on Antimicrobial Susceptibility Testing [EUCAST]: resistant). Each isolate was tested against amikacin (0.25-1024 µg/ml), fosfomycin (0.1-409.6 µg/ml), and amikacin/fosfomycin (5:2 ratio) using CLSI methods (agar dilution with supplements). Control strains included a range of MIC values (amikacin: 0.25-1024 µg/ml; fosfomycin: 0.1-409.6 µg/ml).

For 21 *A. baumannii*, 21 *P. aeruginosa*, and 20 *K. pneumoniae* strains, amikacin (Table 1) and fosfomycin (Table 2) MIC values were reduced with the amikacin/fosfomycin combination. For control stains, 100% of amikacin and 91.7% of fosfomycin MIC values were within published ranges.

For *A. baumannii* strains, the effect was most pronounced for strains with high amikacin resistances (MIC, >1024 µg/ml); for these 5 isolates, amikacin MIC values were reduced to <256 µg/ml with the amikacin/fosfomycin combination. For 11 of 21 *P. aeruginosa* strains, amikacin MIC values remained stable (±one log 2 dilution step) with the addition of fosfomycin. For the other 10 strains, amikacin MIC values decreased>fourfold when fosfomycin was added. For 9 of 20 *K. pneumoniae* strains, amikacin MIC values remained stable with the addition of fosfomycin. For the other 11 strains, amikacin MIC values decreased more than fourfold when fosfomycin was added (decrease >32-fold for 6/11 strains).

Figure 4:
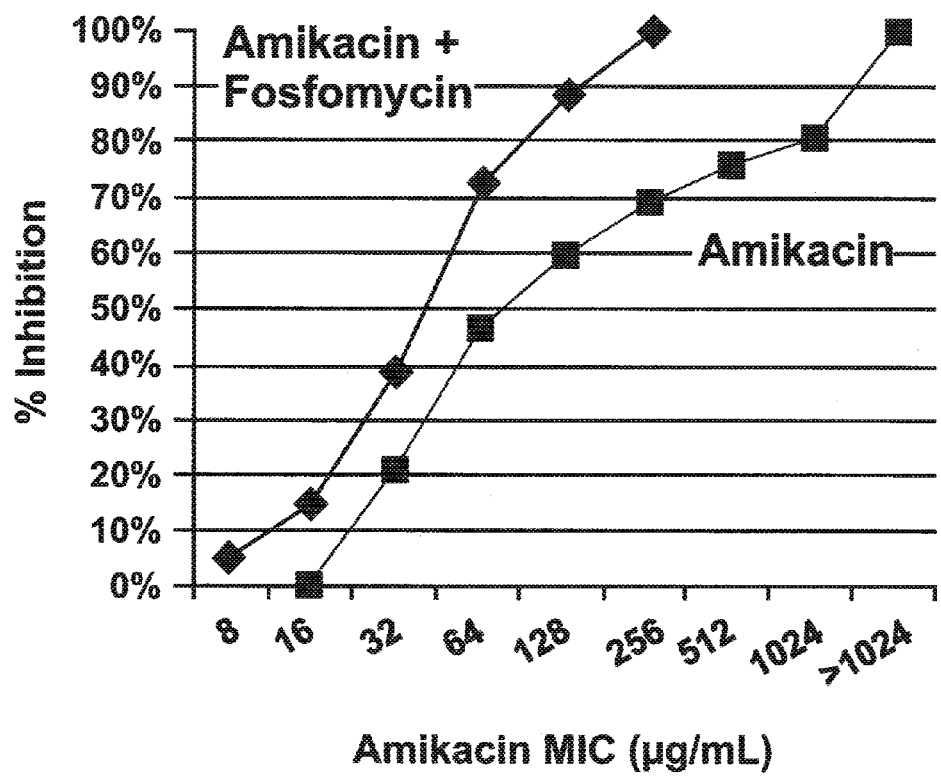
FIG. 4 is a graph of amikacin concentrations against % inhibition showing synergy with fosfomycin.

Overall, median MIC values for amikacin (Table 1) and fosfomycin (Table 2) each decreased twofold with the amikacin/fosfomycin combination. Addition of fosfomycin reduced the amikacin concentration required to inhibit all 62 isolates from >1024 to <256 µg/mL (FIG. 4).

Combining amikacin in a 5:2 ratio with fosfomycin significantly enhanced the potency of amikacin against 62 Gram-negative, amikacin-resistant pathogens. Interactions between amikacin and fosfomycin varied by isolate, and ranged from non-detectable to high-level synergy. These results support development of the amikacin/fosfomycin combination for aerosolized administration where high drug levels can be achieved.

TABLE 1

Amikacin MIC values (±fosfomycin)
Mediana (range) Amikacin MIC, µg/mL
Median (range) Amikacin MIC, µg/mL

| | No. Isolates | Amikacin | Amikacin/Fosfomycin (5:2) |
|---|---|---|---|
| *A. baumannii* | 21 | 8 (32, >1024) | 8 (32, 256) |
| *P. aeruginosa* | 21 | 128 (32, >1024) | 64 (8, 256) |
| *K. pneumoniae* | 20 | 256 (32, >1024) | 32 (16, 128) |
| All | 62 | 128 (32, >1024) | 64 (8, 256) | a. Median = MIC50; Mediana (range) Amikacin MIC; µg/mL; Median' (range) Amikacin MIC, µg/ml

TABLE 2

Fosfomycin MIC values (±amikacin)
Median$^a$ (range) Fosfomycin MIC; µg/mL

| | No. Isolates | Fosfomycin | Amikacin/Fosfomycin (5:2) |
|---|---|---|---|
| *A. baumannii* | 21 | 204.8 (204.8, 204.8) | 25.6 (12.8, 102.4) |
| *P. aeruginosa* | 21 | 51.2 (3.2, 102.4) | 25.6 (3.2, 102.4) |
| *K. pneumoniae* | 20 | 25.6 (12.8, 204.8) | 12.8 (6.4, 51.2) |
| All | 62 | 51.2 (3.2, 204.8) | 25.6 (3.2, 102.4) |

$^a$Median = MIC50; Mediana (range) Fosfomycin MIC, µg/ml

Example 6

Amikacin Chloride Formulation from Amikacin-Base and pH Balance

Inhalation solutions are designed to be tolerable when administered, and there is substantial literature identifying a few critical parameters that influence tolerability. The pH of the solution, the osmolality of the solution, and the presence of permeable anions in the solution all determine whether a solution can be acceptably delivered to the lungs without triggering adverse reactions (cough, bronchospasms, etc).

A two-part formulation of amikacin and fosfomycin (which is mixed immediately prior to use) was designed so that the final mixed solution would be as close to neutral in pH as possible, while maximizing the stability of each component. Fosfomycin is most stable under basic conditions, which requires the amikacin solution to be lower in pH, so that the resulting mixture is neutral.

An acidic, citrate-buffered formulation of amikacin (based on the commercial injectable formulation) was compared to an unbuffered formulation at pH 7. A mixture experiment was performed by mixing each into fosfomycin solutions at increasingly basic pH values (which enhance the solutions stability of fosfomycin). Results are in Table 3.

TABLE 3

Final solution pH after mixing of 40 mg/mL Fosfomycin with 100 mg/mL Amikacin

|  | Fosfomycin pH 8 | Fosfomycin pH 9 | Fosfomycin pH 10 |
|---|---|---|---|
| Amkacin, 100 mg/mL, pH 7 (WFI) | 7.51 | 7.55 | 7.56 |
| Amikacin, 100 mg/mL, pH 5.5 (citrate) | 6.82 | 6.87 | 6.86 |

Another formulation uses fosfomycin disodium as a powder mixed with the amikacin solutions. The two amikacin formulations were mixed with the appropriate amount of fosfomycin disodium powder and the resulting solution pH was evaluated. Results are in Table 4.

TABLE 4

Final solution pH after mixing of 200 mg of Fosfomycin with 8 mL of Amikacin at 50 mg/mL

|  | ~210 mg Fosfomycin disodium powder |
|---|---|
| Amkacin, 50 mg/mL, pH 7 (WFI) | 7.58 |
| Amikacin, 50 mg/mL, pH 5.5 (citrate) | 6.87 |

The data show that all final solutions fall within a pH range considered tolerable with the lung physiology (~4.2-8.0). Amikacin at pH 7 when mixed with fosfomycin at pH 8, 9, or 10, produces a final solution pH of 7.51-7.56. Fosfomycin is increasingly stable as the pH becomes more basic. Therefore, more basic formulations of fosfomycin can be created if needed.

The data also support a powder formulation comprising amikacin solutions mixed with the required amount of fosfomycin disodium powder to yield a resulting solution with an acceptable pH (6.87-7.58).

A two-part liquid formulation with the amikacin component at a neutral pH is also beneficial and would be well tolerated by a patient.

Example 7

Manufacturing Plan for Amikacin/Fosfomycin Combination

The Amikacin Fosfomycin Inhalation System (AFIS) consists of amikacin solution (AMS) (3 mL sterile unit dose ampoule, 100 mg/mL), fosfomycin solution (FFS) (3 mL sterile unit dose ampoule, 40 mg/mL) and the PARI Investigational eFlow® Inline Nebulizer System. AMS and FFS were dispensed to the nebulizer reservoir to create the Amikacin Fosfomycin Admixture (AFA). The nebulizer delivered the aerosolized AFA directly into the inspiratory arm of a ventilator for patients receiving mechanical ventilation.

Amikacin Base, EP is compendial (Ph Eur) and is manufactured by ACS Dobfar S.p.a under DMF 13762. The API is manufactured in Bergamo, Italy. Fosfomycin Disodium is compendial (Ph Eur) and is manufactured by Ercros, S.A. under DMF 14341. The API is manufactured in Madrid, Spain. Rather than commercial amikacin sulfate, the amikacin base is the starting material. Amikacin base has a pH of approximately 11, and large amounts of HCl are required to neutralize the pH. In the two-part formulation (used to combine with equal volumes of 40 mg/mL fosfomycin to generate the final formulation of 50 mg/mL amikacin, 20 mg/mL fosfomycin), the amikacin 100 mg/mL solution has a final pH of 7.5-7.6 and has an osmolality of approximately 533 mOsmol/kg, of which only approximately 170 mOsmol/kg is due to the amikacin, the balance is from the chloride anion. This concentration of chloride anion provides the permeant anion that will prevent cough.

In contrast, the starting pH of amikacin sulfate is 3.5-5.5 and little or no HCl is needed to neutralize the pH of the solution. Note that in the Neiderman paper (supra) amikacin sulfate was delivered as an aerosol to patients with VAP, and bronchospasm was reported in some patients. In contrast, none was seen in the study presented in Example 3. As described above, a final formulation has an amikacin concentration of 50 mg/ml and chloride anion concentration of approximately 265 meq/liter. The low end of an acceptable range would be an amikacin concentration of 25 mg/ml and chloride anion concentration of approximately 130 meq/liter; however, as low as 30 meq/liter could be used with another anion in addition to chloride. The high end of the amikacin concentration would be 100 mg/ml and a chloride anion concentration of approximately 540 meq/liter. This formulation yields an osmolality of 900 mOsmol/L, and any increase would prevent dilution of the formulation with humidity sufficient to make it tolerable.

Figure 5:
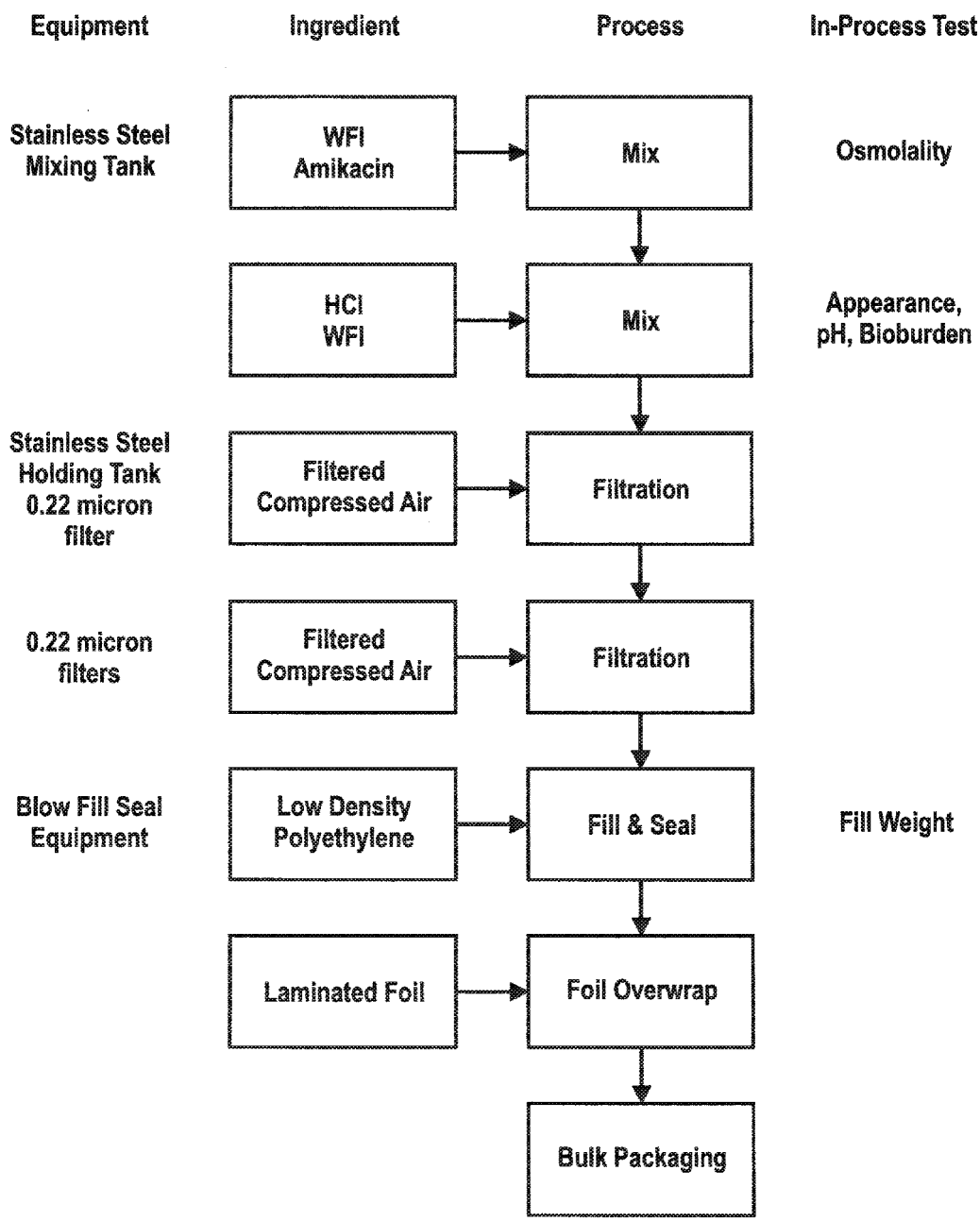
FIG. 5 is a flow diagram of the manufacturing steps of the amikacin solution.

The flow diagram depicting the steps of the manufacturing process of amikacin solution is provided in FIG. 5. The flow diagram indicates where each raw material enters the manufacturing process.

The amikacin solution is manufactured as follows:
1. Add the calculated amount of Water for Injection (WFI) to the stainless steel tank.
2. Add the calculated amount of amikacin to the tank and mix until dissolved.
3. Add 90% of the calculated amount of HCl and mix for 5-10 minutes.
4. Titrate the amikacin-HCl solution with remaining HCl until solution reaches pH 7.0±0.3.
5. Bring the solution to final mass with WFI and mix for 10-15 minutes.
6. Filter the solution through a 0.22 micron filter into a holding tank.
7. Filter the solution through two 0.22 micro filters in series.
8. Use Blow/Fill/Seal equipment to form the LDPE ampoule, fill to a target weight and then seal the ampoule.
9. Perform 100% visual inspection and integrity testing on LDPE ampoule.

10. Foil overwrap ampoules individually.
11. Perform 100% leak detection on foil overwrapped ampoules.

The flow diagram depicting the steps of the manufacturing process of fosfomycin solution is provided in FIG. 6. The flow diagram indicates where each raw material enters the manufacturing process.

The fosfomycin solution is manufactured as follows:
1. Add the calculated amount of WFI to the stainless steel tank.
2. Add the calculated amount of fosfomycin to the tank and mix until dissolved.
3. Add 90% of the calculated amount of HCl and mix for 5-10 minutes.
4. Titrate the solution with remaining HCl until solution reaches pH 8.0±0.3.
5. Bring the solution to final mass with WFI and mix for 10-15 minutes.
6. Filter the solution through a 0.22 micron filter into a holding tank.
7. Filter the solution through two 0.22 micro filters in series.
8. Use Blow/Fill/Seal equipment to form the LDPE ampoule; fill to a target weight; and then seal the ampoule.
9. Perform 100% visual inspection and integrity testing on LDPE ampoule.
10. Foil overwrap ampoules individually.
11. Perform 100% leak detection on foil overwrapped ampoules.

Option 1—Use Phase 2 Manufacturing Process

In a scaled-up commercial the manufacturing process may be transferred to other contract manufacturing sites that specialize in Blow/Fill/Seal technology.

Such that both solutions will be contained in one overwrapped ampoule having dual chambers and a single opening. In use, both solutions will be dispensed into the nebulizer at the same time.

All references cited herein are specifically incorporated by reference.

What is claimed is:

1. A system comprising: a mechanical ventilator comprising:
an airway for transmitting positive air pressure generated by the ventilator to a patient, a source for humidified air operably connected to the airway, and an airway inlet fixture;
an in-line nebulizer operably connected to the airway at the airway inlet fixture, wherein the nebulizer comprises a reservoir containing a combination of amikacin and fosfomycin at a ratio of amikacin to fosfomycin greater than 1.0:1.0 in a hypertonic saline solution having at least about 30 equil/L permeant anion and a vibrating plate membrane having a plurality of apertures with a diameter less than 2.5 microns.

2. The system of claim 1, wherein the nebulizer has an inlet and an outlet each operably connected and sealed at the airway inlet fixture such that the nebulizer does not introduce additional air into the airway.

3. The system of claim 1, wherein the airway inlet fixture is disposed proximal to a ventilator wye piece.

4. The system of claim 1, wherein the in-line nebulizer has an annular vent space surrounding the vibrating plate membrane.

5. The system of claim 1, wherein the in-line nebulizer operates in a continuous mode to generate an aerosol mist.

6. The system of claim 1, further comprising an aerosol mist of the hypertonic solution having a mean particle size less than 5 microns and an osmolality less than 800 mOsmol/L.

7. The system of claim 1, wherein the reservoir contains between about 100 and about 300 mg fosfomycin and between about 150 and 650 mg amikacin.

8. The system of claim 1, further comprising a mixture of humidified air and the aerosol mist within the airway and distal to the in-line nebulizer.

9. The system of claim 8, further comprising an electric control unit to trigger administration of the mixture upon inspiration by the patient.

\* \* \* \* \*